US00PP19661P2

(12) United States Plant Patent
Kerley et al.

(10) Patent No.: US PP19,661 P2
(45) Date of Patent: Jan. 27, 2009

(54) ***PETUNIA×HYBRIDA* PLANT NAMED 'KERBLUFAN'**

(50) Latin Name: *Petunia×hybrida*
Varietal Denomination: Kerblufan

(76) Inventors: David W. Kerley, Bethany, 49 Station Road, Over, Cambridge, CB24 5NJ (GB); Priscilla G. Kerley, Bethany, 49 Station Road, Over, Cambridge, CB24 5NJ (GB)

( * ) Notice: Subject to any disclaimer, the term of this patent is extended or adjusted under 35 U.S.C. 154(b) by 198 days.

(21) Appl. No.: 11/656,779

(22) Filed: Jan. 23, 2007

(51) Int. Cl.
*A01H 5/00* (2006.01)

(52) U.S. Cl. ..... Plt./356

(58) Field of Classification Search ..... Plt./356
See application file for complete search history.

*Primary Examiner*—Howard J Locker
(74) *Attorney, Agent, or Firm*—Audrey Charles

(57) ABSTRACT

A new and distinct cultivar of *Petunia* plant named 'Kerblufan', characterized by its blue-colored flowers, medium green-colored foliage, and moderately vigorous, spreading, and semi-trailing growth habit.

1 Drawing Sheet

Latin name of genus and species of plant claimed: *Petunia×hybrida.*
Variety denomination: 'Kerblufan'.

BACKGROUND OF THE INVENTION

The present invention relates to a new and distinct cultivar of *Petunia* plant botanically known as *Petunia×hybrida* and hereinafter referred to by the cultivar name 'Kerblufan'.

The new cultivar originated in a controlled breeding program in Cambridge, England during August 2002. The objective of the breeding program was the development of early and large flowered *Petunia* varieties.

The new *Petunia* cultivar is the result of cross-pollination. The female (seed) parent of the new cultivar is the proprietary *Petunia×hybrida* breeding selection designated 02-14-3, not patented, characterized by its blue-colored flowers, dark-green-colored foliage, and semi-trailing growth habit. The male (pollen) parent of the new cultivar is the proprietary *Petunia×hybrida* breeding selection designated 02-37-18, not patented, characterized by its dark blue-colored flowers with white tips, medium green-colored foliage, and upright growth habit. The new cultivar was discovered and selected as a single flowering plant within the progeny of the above stated cross-pollination during May 2003 in a controlled environment at Cambridge, England.

Asexual reproduction of the new cultivar by terminal stem cuttings since September 2003 at Cambridge, England has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Kerblufan' as a new and distinct cultivar of *Petunia* plant:

1. Blue-colored flowers;
2. Medium green-colored foliage; and
3. Moderately vigorous, spreading, and semi-trailing growth habit.

Plants of the new cultivar differ from plants of the female parent primarily in flower size and from plants of the male parent primarily in uniformity of flower color.

Of the many commercially available *Petunia* cultivars known to the inventor, the most similar in comparison to the new cultivar is 'Sunblu', not patented. However, in side by side comparisons, plants of the new cultivar differ from plants of 'Sunblu' in the following characteristics:

1. Plants of the new cultivar have larger flowers than plants of 'Sunblu'; and
2. Plants of the new cultivar have a bluer flower color than plants of 'Sunblu'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Kerblufan'. The plants were grown in 8-inch hanging pots with three plants per pot for about 12 weeks in a greenhouse at Cambridge, England.

DETAILED BOTANICAL DESCRIPTION

Figure 1:
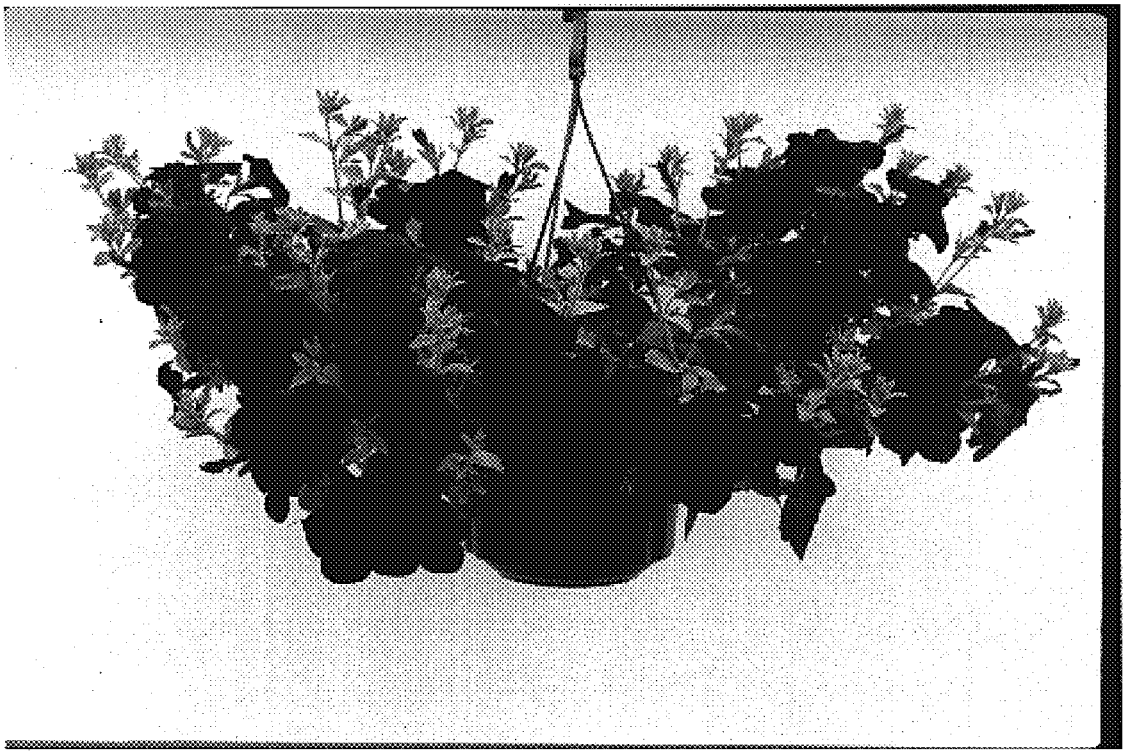
FIG. 1 illustrates a side view of the overall growth and flowering habit of 'Kerblufan'.
Figure 2:
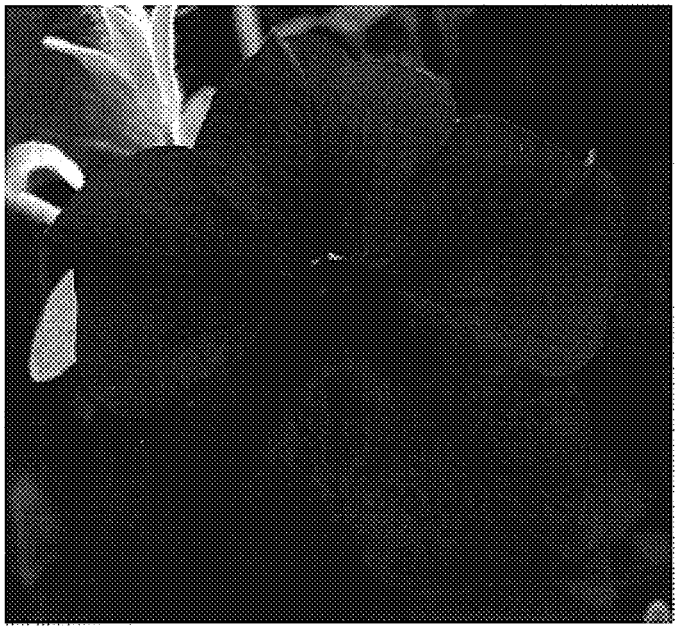
FIG. 2 illustrates a close-up view of an individual flower of 'Kerblufan'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 1995 edition, except where general color terms of ordinary significance are used. The color values were determined on Sep. 20, 2006 between 10.00 a.m. and 12.00 p.m. under natural light conditions in Cambridge, England.

The following descriptions and measurements describe plants produced from cuttings taken from stock plants and grown in a glass-covered greenhouse under conditions comparable to those used in commercial practice. The plants were grown at Cambridge, England in 8-inch hanging pots for 12 weeks utilizing a soilless growth medium. Greenhouse temperatures were maintained at approximately 64° F. to 95° F. (18° C. to 35° C.) during the day and approximately 57° F. to 68° F. (14° C. to 20° C.) during the night. Greenhouse light levels of 3,200 footcandles to 6,000 footcandles were maintained during the day.

Botanical classification: *Petunia×hybrida* cultivar Kerblufan.

Parentage:

*Female parent.*—Proprietary *Petunia×hybrida* breeding selection designated 02-14-3.

*Male parent.*—Proprietary *Petunia×hybrida* breeding selection designated 02-37-18.

Propagation:

*Type cutting.*—Terminal stem.

*Time to initiate roots.*—Approximately 10 days.

*Time to produce a rooted cutting.*—Approximately 28 to 35 days.

*Root description.*—Fibrous.

*Rooting habit.*—Freely branching.

Plant description:

*Commercial crop time.*—Approximately 5 to 7 weeks from a rooted cutting.

*Growth habit and general appearance.*—Spreading, semi-trailing.

*Size.*—Height from soil level to top of plant plane: Approximately 20.0 cm. Width: Approximately 60.0 cm.

*Branching habit.*—Freely branching; however, one pinch is required for commercial product. Quantity of main branches per plant: Approximately 4 to 5.

*Branch.*—Length: Approximately 61.3 cm. Diameter: Approximately 2.5 mm. Length of central internode: Approximately 4.5 cm. Texture: Pubescent. Color of mature stem: 144A.

Foliage description:

*General description.*—Fragrance: Not noticeable. Form: Simple. Arrangement on non-flowering stem: Alternate. Arrangement on flowering stem: Opposite.

*Leaves.*—Aspect: Perpendicular to obtuse angle to stem. Shape: Elliptic. Margin: Entire, often with one undulation. Apex: Acute. Base: Attenuate. Venation pattern: Pinnate. Length of mature leaf: Approximately 5.7 cm. Width of mature leaf: Approximately 3.4 cm. Texture of upper surface: Slightly pubescence. Texture of lower surface: Slightly pubescence, particularly on venation. Color of upper surface of young foliage: 137A to 137B with venation of 144A. Color of lower surface of young foliage: 137C with venation of 144A. Color of upper surface of mature foliage: 137A with venation of 144A. Color of lower surface of mature foliage: 146B with venation of 144A.

*Petiole.*—Length: Approximately 4.7 mm. Width: Approximately 2.0 mm. Texture: Pubescent. Color upper surface: 144A. Color lower surface: 144B.

Flowering description:

*Flowering habit.*—'Kerblufan' is freely flowering under outdoor growing conditions with substantially continuous blooming from spring through autumn and year-round in greenhouse environment.

*Lastingness of individual flower on the plant.*—Approximately 10 to 12 days, flowers not persistent.

Flower description:

*General description.*—Type: Salverform. Arrangement: Flowers face outward; single, axillary. Fragrance: Not noticeable.

*Bud.*—Rate of opening: Generally takes 2 to 3 days for bud to progress from first color to fully open flower.

*Bud just before opening.*—Shape: Closest to ovate. Length: Approximately 2.9 cm. Color: 143C to 143D and 88B.

*Corolla.*—Diameter: Approximately 7.6 cm. Flower depth: Approximately 4.5 cm.

*Petals.*—Quantity: 5, fused to form a tube. Shape: Roughly spatulate. Appearance: Dull, smooth. Margin: Slightly undulate. Apex: Mucronate. Length from tube: Approximately 3.9 cm. Width: Approximately 3.5 cm. Texture of upper surface: Glabrous, slightly rugose. Texture of lower surface: Slight pubescence, slightly rugose. Color of upper surface when first open: 89A with venation of deeper than 88A. Color of lower surface when first open: 86B with venation of 144B. Color of upper surface when fully open: 88A with venation deeper than 88A. Color of lower surface when fully open: 82A with venation of 144B.

*Corolla tube.*—Length: Approximately 2.4 cm. Diameter at distal end: Approximately 1.1 cm. Diameter at proximal end: Approximately 4.3 mm. Texture of inner surface: Fairly smooth. Texture of outer surface: Pubescent, somewhat coarse. Color of inner surface: 83B with venation of deeper than 88A. Color of outer surface: 84A with venation of 90A

*Peduncle.*—Strength: Moderate. Aspect: Approximately 25 degree to 45 degree angle to stem. Length: Approximately 3.9 cm. Diameter: Approximately 1.5 mm. Texture: Pubescent. Color: 144A.

*Sepals.*—Quantity per flower: 5, fused at base. Shape: Narrow oblong, slightly undulating margin. Apex: Obtuse. Length: Approximately 2.4 cm. Width: Approximately 7.1 mm. Texture of upper and lower surfaces: Pubescent. Color of upper surface: Between 137C and 146B. Color of lower surface: Between 137D and 146D.

*Reproductive organs.*—Androecium: Stamen quantity: 5, partially fused to inside of corolla tube. Anther shape: Bilobed. Anther length: Approximately 2.5 mm. Anther color: 91C. Pollen amount: Abundant. Pollen color: 97C. Gynoecium: Pistil quantity: 1 per flower. Pistil length: Approximately 2.5 cm. Stigma shape: Funnel. Stigma color: Between 138A and 143A. Style length: Approximately 2.3 cm. Style color: 145B with some anthocyanin near the stigma. Ovary color: 145A.

Seed and fruit production: Neither seed nor fruit production has been observed.

Disease and pest resistance: Resistance to pathogens and pests common to *Petunia* has not been observed.

What is claimed is:

1. A new and distinct cultivar of *Petunia* plant named 'Kerblufan', substantially as herein shown and described.

* * * * *